United States Patent [19]

Laird et al.

[11] Patent Number: 5,288,900

[45] Date of Patent: Feb. 22, 1994

[54] CRYSTALLIZATION OF OPTICAL ISOMERS OF LEUKOTRIENE ANTAGONISTS USING (R)-4-NITRO-α-METHYLBENEZENEMETHONAMINE

[75] Inventors: Trevor Laird, Mayfield, England; Robert J. Mills, Norristown, Pa.

[73] Assignee: Smithkline Beecham Corporation, Philadelphia, Pa.

[21] Appl. No.: 30,076

[22] PCT Filed: Sep. 20, 1991

[86] PCT No.: PCT/US91/06862

§ 371 Date: Apr. 22, 1993

§ 102(e) Date: Apr. 22, 1993

[87] PCT Pub. No.: WO92/05151

PCT Pub. Date: Apr. 2, 1992

[51] Int. Cl.$^5$ .................. C07B 57/00; C07C 317/06; C07C 323/16; C07D 257/04; C07D 307/02

[52] U.S. Cl. .................... 562/401; 548/253; 549/496; 560/11; 560/15; 562/406; 562/429

[58] Field of Search .......... 562/401, 426, 429; 549/496; 548/253; 560/11, 15; 564/154

[56] References Cited

U.S. PATENT DOCUMENTS

| | | | |
|---|---|---|---|
| 4,820,719 | 4/1989 | Gleason et al. | 562/426 X |
| 4,845,272 | 7/1989 | Nohira et al. | 562/401 |
| 4,904,822 | 2/1990 | Nohira et al. | 562/401 |
| 4,931,587 | 6/1990 | Piselli | 562/401 |
| 4,939,295 | 7/1990 | Merli et al. | 562/401 |

Primary Examiner—José G. Dees
Assistant Examiner—Vera C. Clarke
Attorney, Agent, or Firm—James M. Kanagy; Edward T. Lentz; Stuart R. Suter

[57] ABSTRACT

This invention relates to certain salts of leukotriene antagonists and the use of certain amines to form these salts as a means for selectively crystallizing optical isomers of the leukotriene antagonists recited herein.

24 Claims, No Drawings

CRYSTALLIZATION OF OPTICAL ISOMERS OF LEUKOTRIENE ANTAGONISTS USING (R)-4-NITRO-α-METHYLBENEZENEMETHONAMINE

SCOPE OF THE INVENTION

This invention relates to certain amine salts of leukotriene antagonists and the use of certain amines to form these salts as a means for crystallizing selectively optical isomers of the leukotriene antagonists recited herein.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

Antagonists to SRS substances have been developed in an attempt to provide relief from the disease conditions giving rise to or resulting from these compounds. A number of the compounds developed are normally prepared as a racemic mixture, though activity lies primarily or completely in just one of the optical isomers. Resolving these mixtures is a useful, if not necessary step in preparing a useful formulation for treating these diseases. It has now been found that for certain compounds, the ones set out below, this can be accomplished most readily and inexpensively by means of (R)-4-nitro-α-methylbenzenemethanamine. This amine is uniquely suited to resolving certain enantiomers of the compounds given below so that the most active isomer can be obtained for use in treating SRS-related diseases.

DETAILED DESCRIPTION OF THE INVENTION

The compounds of this invention are (R)-4-nitro-α-methylbenzenemethanamine salts of formula I

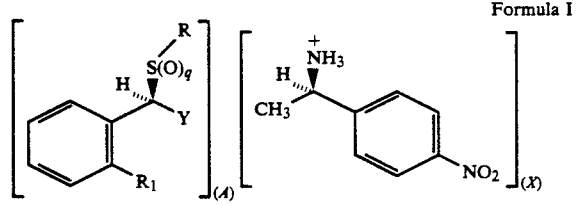

Formula I where:
A is 1 and X is 1 or 2;
$R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;
q is 0, 1 or 2, with the proviso that $R_1$ is not alkylthio or phenylthioalkyl when q is 1 or 2;
Y is $COR_3$, $C(R_4)H(CH_2)_mCOR_3$, or $(CH_2)_{0-1}$-C-tetrazolyl;
$R_3$ is $O^-$, amino, or $C_1$ to $C_6$ alkoxy,
$R_4$ is hydrogen, methyl, $C_1$ to $C_4$-alkoxy, fluoro or hydroxy;
m is 0, 1, or 2;
R is $(CH_2)_nCOR_6$;
n is 0 to 6;
$R_6$ is $O^-$, amino, or $C_1$ to $C_6$-alkoxy;
with the proviso that at least one of Y or R must have an $R_3$ or $R_6$ group respectively which is $O^-$.

This invention also relates to a process for separating a single isomer, either the R or S form, from a racemic mixture of a compound of formula II

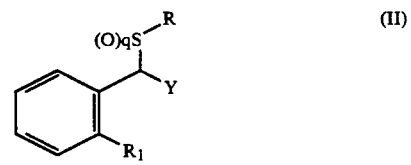

where R, $R_1$, q and Y are defined above with the proviso that $R_3$ and $R_6$ are $R_{3'}$ and $R_{6'}$ where $R_{3'}$ and $R_{6'}$ are independently —OH, amino, or $C_1$ to $C_6$ alkoxy, with the further proviso that at least one of $R_{3'}$ or $R_{6'}$ must be —OH or a salt thereof, which process comprises treating a racemic mixture of formula II with about 0.5 to 2.5 equivalents, relative to the number of carboxylic acid groups in the formula, of either (R)-4-nitro-α-methylbenzenemethanamine or (S)-4-nitro-α-methylbenzenemethanamine, recovering a crystalline salt, and converting the salt to an acid or a pharmaceutically acceptable salt. It is preferred to use 0.5 to 1.5 equivalents of the nitro compound per carboxylic acid group in formula II. This process yields a substantially pure single enantiomer from a racemic mixture.

A preferred class of salts are those of formula (IA)

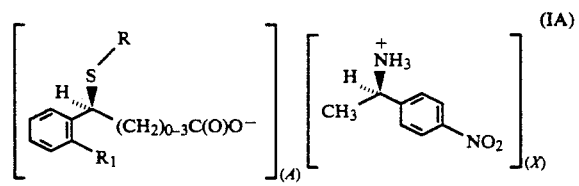

wherein A is 1, X is 1 or 2, and $R_1$ and R are described above.

Another preferred group of these salts are 3-aryl-propionates of formula (IB)

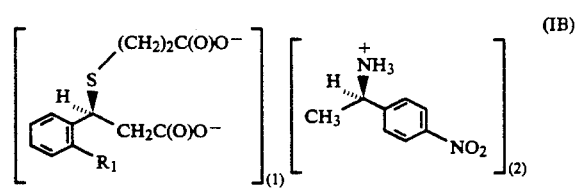

wherein $R_1$ is defined above, particularly where $R_1$ is phenylalkyl. Most preferred among the salts of this group are:
the bis-(R)-4-nitro-α-methylbenzenemethanamine salt of (S)-β-[(2-carboxyethyl)thio]-2-(1-dodecyl)benzenepropanoic acid; and the bis-(R)-4-nitro-α-methylbenzenemethanamine salt of (S)-β-[(2-carboxyethyl)thio]-2-(8-phenyloctyl)benzenepropanoic acid.

Another preferred group of salts are the aryl-acetates of formula (IC).

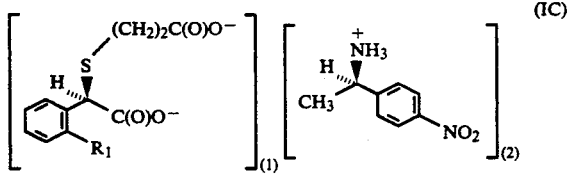

where $R_1$ is described above, particularly where $R_1$ is phenylalkyl.

The salts of the formula (IC) are exemplified by the following compounds:
the bis-(R)-4-nitro-α-methylbenzenemethanamine salt of (R)-α-[(2-carboxyethyl)thio]-2-(1-dodecyl)benzeneacetic acid; and the
bis-(R)-4-nitro-α-methylbenzenemethanamine salt of (R)-α-[(2-carboxyethyl)thio]-2-(8-phenyloctyl)benzeneacetic acid.

Another preferred group of salts are 3-aryl-2-hydroxypropionates of formula (ID)

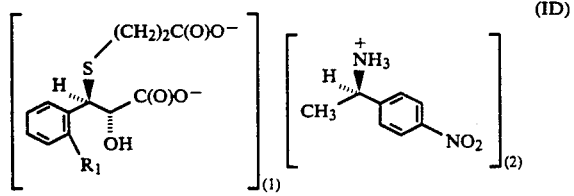

where $R_1$ is defined above, particularly where $R_1$ is phenylalkyl.

The compounds of formula (ID) are exemplified by the following compounds:
the bis-(R)-4-nitro-α-methylbenzenemethanamine salt of [R-(R*,S*)]-β-[(2-carboxyethyl)thio]-α-hydroxy-2-(8-phenyloctyl)benzenepropanoic acid; and the
bis-(R)-4-nitro-α-methylbenzenemethanamine salt of [R-(R*,S*)]-β-[(2-carboxyethyl)thio]-α-hydroxy-2-(1-dodecyl)benzenepropanoic acid.

In a process for resolving racemates of formula II, the following sets of general and specific compounds are preferred.

A set of preferred racemates are those of formula (IIB),

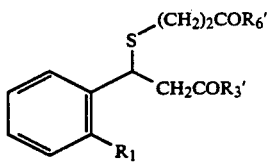

more particularly those where $R_1$ is a phenyl-$C_4$ to $C_4$ to $C_{10}$-alkyl. Most particularly racemates of formula (IIB) can be treated with the (R)-4-nitro-α-methylbenzenemethanamine to obtain, after further manipulation, the isomers (S)-β-[(2-carboxyethyl)thio]-2-(1-dodecyl)-benzenepropanoic acid and (S)-β-[(2-carboxyethyl)thio]-2-(8-phenyloctyl)benzenepropanoic acid.

Another set of preferred racemates are those of formula IIC

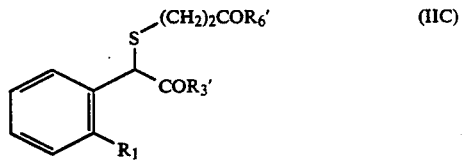

particularly those where $R_1$ is a phenyl-$C_4$ to $C_{10}$ alkyl. Most particularly racemates of formula (IIC) can be treated with (R)-4-nitro-α-methylbenzenemethanamine to obtain, after further manipulation, the isomers (R)-α-[(2-carboxyethyl)thio]-2-(1-dodecyl)benzeneacetic acid and (R)-α-[(2-carboxyethyl)thio]-2-(8-phenyloctyl)benzeneacetic acid.

Yet another preferred set of racemates are the 2S*,3R*-isomers represented by formula (IID),

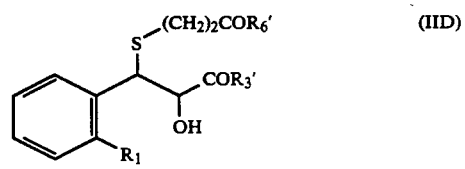

particularly those where $R_1$ is a phenyl-$C_4$ to $C_{10}$-alkyl. Most particularly the racemate of formula (IID) can be treated with (R)-4-nitro-α-methylbenzenemethanamine to obtain, after further manipulation, the isomer [R-(R*,S*)]-β-[(2-carboxyethyl)thio]-β-hydroxy-2-(8-phenyloctyl)benzenepropanoic acid.

The racemates of this invention can be prepared according to the disclosure set out in U.S. Pat. No. 4,820,719 issued Apr. 11, 1989. That disclosure, in full, is incorporated herein by reference as if set out herein.

The amine, (R)-4-nitro-α-methylbenzenemethanamine, can be purchased as a hydrochloride salt from a commercial source such as Chiron, a Norwegian company. Or the hydrochloride salt may be made by the process of Baker, J. W. & Ingold, C. K., J. Chem. Soc., 261–264, 1927, and the R and S isomers fractionally crystallized by the method of Nerdel, F. and Liebeg, H., Ann 621:42–50, 1959. A more recent process for making the hydrochloride salt of this amine is given in Perry, C. W. et al, Synthesis 492–494, 1977. The amine can be prepared by treating the hydrochloride salt with a strong base and extracting the amine into an organic solvent, for example methylene chloride or toluene. Amine prepared in this manner may be stored prior to use. Alternatively, the amine can be liberated in-situ by treating the hydrochloride salt with a strong base in an aqueous alcoholic solvent, and then used immediately.

This amine is a particularly effective resolving agent for separating out a particular isomer from a racemic mixture of compounds denoted by formula II. A salt is formed between the amine and the carboxylate function. This salt can be fractionally crystallized, giving a salt comprising the amine and just one isomer of the acid. An alcohol is the preferred solvent for crystallization. This method provides excellent selectivity for the desired isomer.

These salts may be converted to the corresponding acid by means of a dilute acid. Or they may be converted to another salt, such as an alkali metal salt, by treating a solution of the isolated salt with a base. For example, the salt can be converted to the free acid by treating a solution of that salt with dilute mineral acid, for example 0.5N HCl at room temperature or thereabouts. The mixture is then extracted with an appropriate organic solvent, or subjected to other convenient separatory means, and the pure isomer obtained as the free acid after removing the solvent.

The following examples illustrate the process for making and preparing the compounds of this invention. Being examples they are not to be considered as limiting the invention set forth in the claims appended hereto.

EXAMPLE 1

Preparation of (S)-β-[(2-Carboxyethyl)thio]-2-(8-phenyloctyl)benzenepropanoic acid, compound with (R)-4-Nitro-α-methylbenzenemethanamine (1:2)

Racemic β-[(2-carboxyethyl)thio]-2-(8-phenyloctyl)-benzenepropanoic acid [6.05 g (60.7% assay, 8.3 mmol)] was dissolved in 80 mL of 2-propanol and treated with a solution of 1.48 g (8.9 mmol) of (R)-4-nitro-α-methyl-benzenemethanamine in 2-propanol. The mixture was heated to reflux, then allowed to cool to 0° C. The resulting solids were isolated by filtration to afford, after drying, 2.33 g of crude product. Chiral HPLC analysis indicated 97.7% of the desired S-enantiomer. After recrystallizing from 2-propanol, the content of S-enantiomer was enhanced to >99.5%. The salt contained 2 moles of amine per mole of diacid: Mp 239°–240° C.; $[α]_D^{25} = -8.9°$ (c=1.0, methanol); Chiral HPLC (Bakerbond Chiralcel OD, 4.6 mm×250 mm, 3.5/96.5/0.1 isopropanol/n-hexane/trifluoroacetic acid, 2.0 mL/min, ambient temperature, UV detection at 215 nm): Retention Time=15.9 min (minor peak; R-enantiomer), Retention Time=19.4 min (major peak; S-enantiomer); Anal. Calcd for $C_{42}H_{54}N_4O_8S$: C, 65.09; H, 7.02; N, 7.23; S, 4.14. Found: C, 65.11; H, 7.00; N, 7.39; S, 4.09; $^1$H NMR (CDCl$_3$/CD$_3$OD, 270 MHz) δ 8.21–8.24 (m, 4H), 7.57–7.60 (m, 4H), 7.14–7.39 (m, 9H), 4.47–4.53 (t, 1H), 4.30–4.38 (q, 2H, J=6.6 Hz), 2.32–2.91 (m, 10H), 1.32–1.60 (br, 18H).

EXAMPLE 2

Preparation of [R-(R*,S*)]-β-[(2-Carboxyethyl)thio]-α-hydroxy-2-(8-phenyloctyl)benzenepropanoic acid, compound with (R)-4-Nitro-α-methylbenzenemethanamine,(1:2)

A solution of racemic (R*,S*)-β-[(2-carboxyethyl)-thio]-α-hydroxy-2-(8-phenyloctyl)benzenepropanoic acid (2.32 g, 6.6 mmol) was prepared by warming the acid in 40 mL of 2-propanol. The resulting solution was treated with 2.32 g (13.9 mmol) of (R)-4-nitro-α-methyl-benzenemethanamine in 50 mL of absolute ethanol. The solution was heated to reflux, then cooled to room temperature. The resulting solids were isolated by filtration to afford, after drying, 1.95 g of crude product. Chiral HPLC analysis indicated 95.2% of the desired 2S,3R-enantiomer. After recrystallizing from absolute ethanol, the content of 2S,3R-enantiomer was enhanced to >99.5%. The salt contained 2 moles of amine per mole of diacid: Mp 141.5°– 142.5° C.; $[α]_D^{25} = -20.0°$ (c=1.0, methanol); Chiral HPLC (Bakerbond Chiralcel OD, 4.6 mm×250 mm, 10.0/90.0/0.1 isopropanol/n-hexane/trifluoroacetic acid, 2.0 mL/min, ambient temperature, UV detection at 215 nm): Retention Time=6.1 min (minor peak; 2R,3S-enantiomer), Retention Time=9.5 min (major peak; 2S,3R-enantiomer); Anal. Calcd for $C_{42}H_{54}N_4O_9S$: C, 63.78; H, 6.88; N, 7.08; S, 4.05. Found: C, 63.80; H, 6.93; N, 7.12; S, 3.94; $^1$H NMR (DMSO-d$_6$, 270 MHz) δ 8.22–8.16 (m, 4H), 7.70–7.65 (m, 4H), 7.28–7.01 (m, 9H), 4.53 (d, 1H, J=3.4 Hz), 4.33–4.26 (q, 2H, J=6.7 Hz), 4.05 (d, 1H, 3.4 Hz), 2.90–2.84 (m, 1H), 2.66–2.34 (m, 7H), 1.53 (m, 4H), 1.37 (d, 6H, J=6.8 Hz), 1.29 (s, 8H).

EXAMPLE 3

Determination and Confirmation of Absolute Configuration

Both (S)-β-[(2-carboxyethyl)thio]-2-(8-phenyloctyl)-benzenepropanoic acid and [R-(R*,S*)]-β-[(2-carboxyethyl)thio]-α-hydroxy-2-(8-phenyloctyl)benzene-propanoic acid react with two molar equivalents of (R)-4-iodo-α-methylbenzenemethanamine to produce highly crystalline salts. In each of these salts, the absolute configuration of the diacid portion was determined unambiguously by single crystal x-ray analysis.

In order to correlate this information to the salts obtained in Examples 1 and 2, each salt was treated with aqueous acid and extracted with ethyl acetate. By analyzing the extracts on an HPLC column (cellulose tris-3,5-dimethylphenylcarbamate chiral stationary phase, coated on silica gel) and comparing retention times to authentic samples of the racemates, it was determined that the diacid portion of the salt from Example 1 possessed the S-configuration, and the diacid portion of the salt from Example 2 possessed the 2S,3R-configuration.

We claim:

1. A salt of formula I

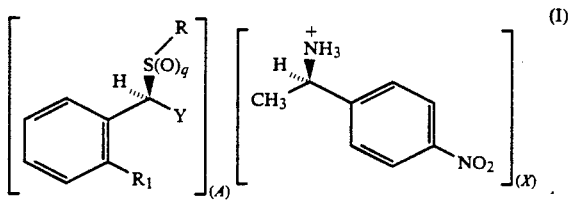

where:

A is 1 and X is 1 or 2;

$R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl unsubstituted or monosubstituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;

q is 0, 1 or 2, with the proviso that $R_1$ is not alkylthio or phenylthioalkyl when q is 1 or 2;

Y is $COR_3$, $C(R_4)H(CH_2)_mCOR_3$, or $(CH_2)_{0-1}$-C-tetrazolyl;

$R_3$ is $O^-$, amino, or $C_1$ to $C_6$ alkoxy, $R_4$ is hydrogen, methyl, $C_1$ to $C_4$-alkoxy, fluoro or hydroxy;

m is 0, 1, or 2;

R is $(CH_2)_nCOR_6$;

n is 0 to 6;

$R_6$ is $O^-$, amino, or $C_1$ to $C_6$-alkoxy;

with the proviso that at least one of Y or R must have an $R_3$ or $R_6$ group respectively which is $O^-$.

2. A salt of claim 1 represented by formula (IA).

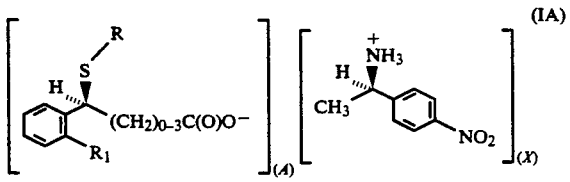

where R₁ is phenylalkyl.

3. A salt of claim 2 where R is $(CH_2)_{1-3}COR_6$.

4. A salt of claim 3 represented by the 3-arylpropionate of formula (IB).

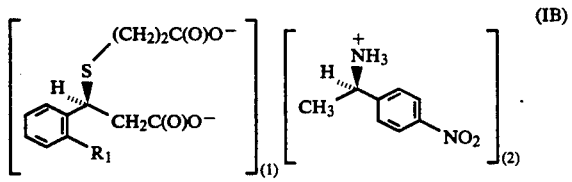

5. A salt of claim 4 where R₁ is phenyl-C₄ to C₁₀ alkyl or C₈ to C₁₃ alkyl.

6. A salt of claim 5 which is the bis-(R)-4-nitro-α-methylbenzenemethanamine salt of (S)-β-[(2-carboxyethyl)thio]-2-(1-dodecyl)benzenepropanoic acid.

7. A salt of claim 5 which is the bis-(R)-4-nitro-α-methylbenzenemethanamine salt of (S)-β-[(2-carboxyethyl)thio]-2-(8-phenyloctyl)benzenepropanoic acid.

8. A salt of claim 3 represented by formula (IC).

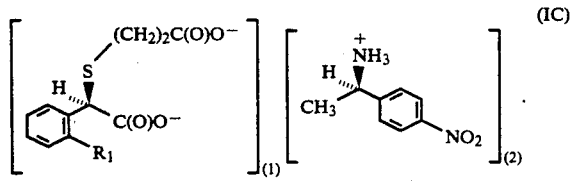

9. A salt of claim 8 where R₁ is a phenyl-C₄ to C₁₀ alkyl or C₈ to C₁₃ alkyl.

10. A salt of claim 9 which is the bis-(R)-4-nitro-α-methylbenzenemethanamine salt of (R)-α-[(2-carboxyethyl)thio]-2-(1-dodecyl)benzeneacetic acid.

11. A salt of claim 9 which is the bis-(R)-4-nitro-α-methylbenzenemethanamine salt of (R)-α-[(2-carboxyethyl)thio]-2-(8-phenyloctyl)benzeneacetic acid.

12. A salt of claim 1 represented by formula (ID).

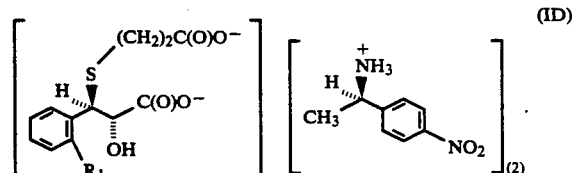

13. A salt of claim 12 where R₁ is a phenyl-C₄ to C₁₀-alkyl.

14. A salt of claim 13 which is the bis-(R)-4-nitro-α-methylbenzenemethanamine salt of [R-(R*,S*)]-β-[(2-carboxyethyl)thio]-α-hydroxy-2-(8-phenyloctyl)benzenepropanoic acid.

15. A process for separating a single isomer from a racemic mixture of a compound of formula II

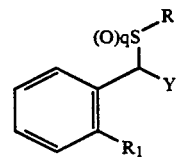

where:
R₁ is C₈ to C₁₃ alkyl, C₇ to C₁₂ alkoxy, C₇ to C₁₂ alkylthio, C₁₀ to C₁₂ 1-alkynyl, 10-undecynyloxy, 11-dodecynyl, phenyl-C₄ to C₁₀ alkyl, phenyl-C₃ to C₉ alkoxy, phenylthio-C₃ to C₉ alkyl with the phenyl optionally mono substituted with bromo, chloro, trifluoromethyl, C₁ to C₄ alkoxy, methylthio or trifluoromethylthio, furyl-C₄ to C₁₀ alkyl, trifluoromethyl-C₇ to C₁₂ alkyl or cyclohexyl-C₄ to C₁₀ alkyl;

q is 0, 1 or 2, with the proviso that R₁ is not alkylthio or phenylthioalkyl when q is 1 or 2;

Y is $COR_{3'}$, $C(R_4)H(CH_2)_m COR_{3'}$, or $(CH_2)_{0-1}$-C-tetrazolyl;

R₃' is OH, amino, or C₁ to C₆ alkoxy,

R₄ is hydrogen, methyl, C₁ to C₄-alkoxy, fluoro or hydroxy;

m is 0, 1, or 2;

R is $(CH_2)_n COR_{6'}$;

n is 0 to 6;

R₆' is OH, amino, or C₁ to C₆-alkoxy;

with the proviso that at least one of R₃' or R₆' is —OH or a salt thereof, which process comprises:

(i). treating a racemic mixture of formula II with between about 0.5 to 2.5 equivalents, relative to the number of carboxylic acid groups in formula (II), of (R)-4-nitro-α-methylbenzenemethanamine;

(ii). recovering a crystalline salt, and (iii). converting the salt to an acid or a pharmaceutically acceptable salt.

16. The process of claim 15 where the separated isomer is a compound of formula

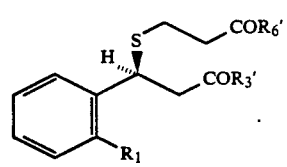

17. The process of claim 16 where R₁ is a phenyl-C₄ to C₁₀-alkyl or C₈ to C₁₃ alkyl.

18. The process of claim 17 which gives the isomer (S)-β-[(2-carboxyethyl)thio]-2-(1-dodecyl)benzenepropanoic acid, or (S)-β-[(2-carboxyethyl)thio]-2-(8-phenyloctyl)benzenepropanoic acid.

19. The method of claim 15 where the separated isomer is that of formula

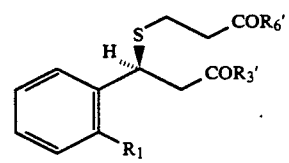

20. The process of claim 19 where $R_1$ is a phenyl-$C_4$ to $C_{10}$ alkyl or $C_8$ to $C_{13}$ alkyl.

21. The process of claim 20 which gives the isomer (R)-α-[(2-carboxyethyl)thio]-2-(dodecyl)benzeneacetic acid or (R)-α-[(2-carboxyethyl)thio]-2-(8-phenyloctyl)-benzeneacetic acid.

22. The process of claim 15 where the separated isomer is represented by the formula

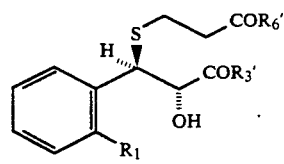

23. The process of claim 22 where $R_1$ is a phenyl-$C_4$ to $C_{10}$-alkyl.

24. The process of claim 23 which gives the isomer [R-(R*,S*)]-β-[(2-carboxyethyl)thio]-α-hydroxy-2-(8-phenyloctyl)benzenepropanoic acid.

* * * * *